United States Patent [19]

Formaro et al.

[11] 4,208,253

[45] Jun. 17, 1980

[54] METHOD FOR MEASURING THE CONCENTRATION OF SODIUM IN A FLOW OF MERCURY-SODIUM AMALGAM

[75] Inventors: Leonardo Formaro; Luciano Cavalli; Artemio Gellera; Marco Fraschini, all of Milan, Italy

[73] Assignee: Euteco S.p.A., Milan, Italy

[21] Appl. No.: 942,238

[22] Filed: Sep. 14, 1978

[51] Int. Cl.² ............................................. G01N 27/46
[52] U.S. Cl. .............................. 204/1 T; 204/195 R; 204/195 H; 204/195 F
[58] Field of Search .................. 204/1 T, 1 A, 195 R, 204/195 H, 195 F

[56] References Cited

U.S. PATENT DOCUMENTS

| | | | |
|---|---|---|---|
| 3,281,348 | 10/1966 | Schumacher et al. | 204/1 A |
| 3,324,013 | 6/1967 | Dewing | 204/1 T |
| 3,480,520 | 11/1969 | Smith | 204/1 A |
| 3,956,094 | 5/1976 | Capuano | 204/195 R |

*Primary Examiner*—T. Tung
*Attorney, Agent, or Firm*—Sughrue, Rothwell, Mion, Zinn and Macpeak

[57] ABSTRACT

The concentration of sodium metal in a flow of mercury-sodium amalgam is measured by flowing an aqueous solution of sodium chloride through a conduit of electrically insulating material terminating with a porous septum or a capillary immersed in the flow of mercury-sodium amalgam, at a rate of at least 4 ml per hour and per cm² of surface area of contact between the surface of the porous septum or the section of the capillary opening and the amalgam, and monitoring the electromotive force generated between said amalgam and a calomel or silver-silver chloride reference electrode located within said conduit and in contact with said solution.

14 Claims, 5 Drawing Figures

METHOD FOR MEASURING THE CONCENTRATION OF SODIUM IN A FLOW OF MERCURY-SODIUM AMALGAM

The invention concerns the measurement of the concentration of sodium in mercury-sodium amalgams.

More particularly the invention concerns a method for measuring continuously the values of the concentration of sodium in a flow of mercury-sodium amalgam by monitoring the electromotive force generated between said amalgam and a reference electrode, a liquid electrolyte being interposed between the said reference electrode and the said amalgam. The reference electrode, the electrolytic liquid and the amalgam form an electrochemical cell, the electromotive force (e.m.f.) of which is a function of the concentration of sodium in the amalgam at the instant at which the said e.m.f. is detected.

This method is particularly useful in the case of electrolytic cells with mercury cathode, employed for the production of chlorine, in which an aqueous solution of sodium chloride is subjected to electrolysis and a continuous flow of sodium amalgam is discharged, from which aqueous sodium hydroxide is subsequently obtained by decomposition of the amalgam with water.

For correct operation of the electrolytic cell, continuous determination of the sodium concentration in the effluent amalgam and the modification of the operating conditions of the cell (by means of suitable controls) when the value of the concentration recorded departs significantly from the nominal chosen value, are required.

This latter value is generally chosen within the range of from 0.15 to 0.50% by weight, principally because concentrations less than 0.15% by weight are not economically convenient, while those greater than 0.5% be weight reduce the flow—characterisitics of the amalgam. The nominal value is generally of the order of 0.2–0.3% by weight.

Thus, the invention provides a method for measuring sodium metal concentration in a flow of mercury-sodium amalgam, characterized by flowing an aqueous solution of sodium chloride through a conduit of electrically insulating material terminating with a porous septum or a capillary immersed in the flow of mercury-sodium amalgam, said solution being passed through said conduit at a rate such as to ensure continuous renewal of the interface between the solution and the amalgam and of at least 4 ml per hour and per cm$^2$ of surface area of contact between the surface of the porous septum or the section of the capillary opening and the amalgam, and monitoring the electromotive force generated between said amalgam and a calomel or silver-silver chloride reference electrode located within said conduit and in contact with said solution, said sodium metal concentration being a univocal function of said electromotive force.

In accordance with a specific embodiment of the present invention the amalgama is the sodium-loaded process-amalgam outflowing from a mercury-chlorine cell having a nominal sodium concentration of from 0.15 to 0.5 wt. %. Preferably, the aqueous solution of sodium chloride has a concentration of from 0.01 M up to saturation at the operating temperature. Under the optimum conditions, the nominal value of the sodium concentration in the effluent amalgam is 0.2–0.3% by weight and the concentration of the sodium chloride in the aqueous solution is 1 M.

As is known, the amalgam discharged from a mercury-chlorine cell, used for the production of chlorine, flows first into a chamber in which it is treated with a small amount of water to remove the chlorides and other impurities, then into a vessel where it forms a hydraulic lock and finally into an amalgam decomposer, in which it is treated with water to transform the sodium contained in the amalgam into the corresponding hydroxide.

According to the present invention the determination of the sodium content in the amalgam can be carried out at any point between the outlet from the electrolytic cell and the inlet to the amalgam decomposer. In a preferred embodiment this determination is carried out in the chamber in which the amalgam is treated with the small amount of water, close to the discharge from this chamber.

The aforesaid conduit is generally a tubular body of electrically insulating material, such as, for example, glass, having an open end and carrying a porous septum or a capillary at the other end. The reference electrode is located within the tubular body at a position intermediate the two ends and is connected to an electrical terminal arranged on the exterior of the tubular body near the open end.

The said electrode may consist of a wire, generally turned into a spiral, made of silver on which silver chloride has been deposited by means of electrolysis.

According to a further embodiment the reference electrode consists of a silver wire, one end of which is in contact with solid silver chloride in the form of granules. These latter are contained in a suitable container of electrically insulating material, generally glass, housed within the tubular body, having several apertures so as to ensure contact of the electrode with the solution of sodium chloride.

In use, the open end of the tubular body is connected to a vessel containing the solution, the end carrying the porous septum or the capillary is immersed in the flow of amalgam and the terminal of the reference electrode is connected to the appropriate input of the measuring means, such as, for example, a millivoltmeter and/or a process computer.

A second electrical wire is provided for the purpose of connecting the second input of the measuring means to a region of the amalgam close to that in which the solution flows.

Preferably, the second electrical wire extends along the conduit from a second terminal located on the exterior of the conduit and near the open end of the latter. The second electrical wire is insulated from the exterior down to a point close to the porous septum or the capillary where it projects from the insulating material and is therefore in direct contact with the amalgam when the septum or capillary is immersed in the said amalgam. Preferably the said second wire is of platinum or of iron.

The calomel electrode is known in the art and generally consists of mercury in contact with a paste of mercury and mercurous chloride, the latter being in contact with the electrolytic solution. A platinum wire is, moreover, in contact with the mercury at one of its ends. The silver-silver chloride electrode may be easily made, for example, from a wire (or a sheet) of silver, on which the silver chloride is formed by means of electrolysis of an aqueous solution of hydrochloric acid.

It should be noted that determinations of the potentials of electrodes consisting of an amalgam of an alkali metal have been carried out for some time. In particular, such potentials have been evaluated in comparison with a reference standard, for example, calomel, or silver-silver chloride such as those described above, the amalgam and the reference electrode being connected by means of an aqueous solution of an alkali metal chloride in typical equipment for an electrochemical cell. However, these techniques have not yet been applied to the continuous determination of the alkali metal content, particularly sodium, in respective amalgams.

In fact those conditions which allow reliable and reproducible results to be obtained over long periods of time such as are necessary in use on a commercial scale have not been found. In fact, it should be noted that chemical changes occur at the interface between the electrolytic liquid and the amalgam with formation of products such as the alkali metal hydroxide and hydrogen. Therefore the values of the potential of the electrode and thus the values of the e.m.f. of the respective electrochemical cell, are altered.

By operating according to the present invention, the disadvantages originating from the said chemical changes are eliminated and it is in this respect that the continuous renewal of the interface between the amalgam and the electrolytic liquid, by means of a continuous flow of the latter in the former, assumes importance.

Thus the concentration of the sodium chloride in the electrolyte constitutes a critical factor and must be maintained rigorously constant during the whole operation. However, the constancy of the feed rate of the electrolyte into the amalgam is not critical, as long as this rate is greater than a minimum value, evaluated experimentally, of 4 ml per hour for each $cm^2$ of surface of contact between the porous septum (or the opening of the capillary) and the amalgam. A particularly suitable rate is 8 ml per hour for each $cm^2$ of the said surface of contact.

The upper limit of the said feed rate is not critical and is dictated by economic considerations and by the necessity of not contaminating the sodium hydroxide finally produced with chlorine ions. By operating under the said conditions, the continuous renewal of the interface which is indespensible for the success of the determination under discussion, is achieved.

It should be noted in this connection that the flow of amalgam is not sufficient to ensure satisfactory renewal of the interface. In fact tests carried out with the amalgam moving but without injection of the electrolyte within the amalgam have not produced any useful results.

The magnitude of the flow of the electrolyte may be controlled, both by means of the head of liquid based on the height of the tank containing the electrolyte with respect to the level of the amalgam, and also through the size of the capillary opening or the characteristics of the porous septum used. In particular the diameter of the capillary opening may conveniently have values of the order of from 0.3 to 1.0 mm. Suitable porous septa are those of sintered glass with pores of from 3 to 150 microns, for example, those known commercially as P1 (pores of 3–15 microns) and P4 (pores of 90–150 microns).

The quantity of the electrolyte which is fed into the amalgam is such as to produce a negligibly low increase (less than 10 ppm) in chlorine ions in the sodium hydroxide finally produced.

In a practical embodiment the amalgam is at a temperature of about 75° C., while the reference electrode is at a temperature of from ambient temperature to a temperature close to that of the amalgam, this depending on the position of the said reference electrode.

Experimentally, no influence has been noted due to this difference in temperature in the case of a silver-silver chloride reference electrode. In the case of the calomel electrode the e.m.f. is influenced by about 0.24 millivolts for each degree centigrade.

It has been found experimentally that, with the said reference electrodes, with a concentration of 1 M up to saturation of the sodium chloride in the electrolytic liquid and with concentrations of the sodium in the amalgam of up to 0.6% by weight, the values of the e.m.f. expressed in volts are generally in the range of from 1.9 to 2.2.

The results of the e.m.f. determinations, in millivolts, effected by using amalgams having a known sodium concentration are shown in Tables 1 to 4.

In particular, the data of Table 1 have been obtained by using a calomel electrode and a silver-silver chloride electrode, and a saturated solution of sodium chloride as the electrolyte, the amalgam being maintained at 75° C. The electrolyte was made to flow into the agitated amalgam through a porous septum of the type P4.

In Table 1 are recorded the values of the concentration of the sodium in the amalgam as a percentage by weight (% Na) determined by an acidimetric method and those of the molar fractions (x Na) multiplied by 1000. The values of the e.m.f. (mV) in the case of the calomel electrode and in the case of the electrode of silver-silver chloride are indicated correspondingly.

Table 1

| % Na | x Na . 1000 | mV (calomel) | mV (Ag/AgCl) |
| --- | --- | --- | --- |
| 0.534 | 44.75 | 2093 | 2036 |
| 0.405 | 34.23 | 2068 | 2015 |
| 0.315 | 26.85 | 2051 | 2001 |
| 0.227 | 19.46 | 2035 | 1983 |
| 0.147 | 12.67 | 2015 | 1962 |
| 0.063 | 5.45 | 1988 | 1931 |
| 0.023 | 2.03 | 1954 | 1896 |

The results of similar tests in which 1 M aqueous sodium chloride is used as the electrolyte, are recorded in Table 2.

Table 2

| % Na | x Na . 1000 | mV (calomel) | mV (Ag/AgCl) |
| --- | --- | --- | --- |
| 0.520 | 43.65 | 2165 | 2157 |
| 0.327 | 27.85 | 2137 | 2127 |
| 0.241 | 20.70 | 2122 | 2112 |
| 0.140 | 12.06 | 2097 | 2087 |
| 0.070 | 6.13 | 2073 | 2061 |
| 0.033 | 2.90 | 2047 | 2032 |

The results of tests similar to the preceding ones in which 1 M aqueous sodium chloride is used as the electrolyte and in which the amalgam is maintained at a temperature of 25° C., are recorded in Table 3.

Table 3

| % Na | x Na . 1000 | mV (calomel) | mV (Ag/AgCl) |
| --- | --- | --- | --- |
| 0.593 | 49.40 | 2112 | 2170 |
| 0.312 | 26.70 | 2178 | 2135 |
| 0.146 | 12.55 | 2142 | 2100 |
| 0.059 | 5.10 | 2113 | 2071 |

The results of tests similar to the preceding ones in which 1 M aqueous sodium chloride as the electrolyte is made to flow into the amalgam maintained at 75° C., through a Teflon capillary having a diameter of the outlet opening of 0.47 mm, are recorded in Table 4.

Table 4

| % Na | X Na . 1000 | mV (Ag/AgCl) |
|---|---|---|
| 0.589 | 49.1 | 2167 |
| 0.520 | 43.65 | 2157 |
| 0.482 | 39.0 | 2149.5 |
| 0.407 | 34.48 | 2139 |
| 0.327 | 27.85 | 2127 |
| 0.242 | 20.7 | 2112 |
| 0.196 | 16.8 | 2101 |
| 0.142 | 12.15 | 2087 |
| 0.127 | 11.0 | 2082.5 |
| 0.099 | 8.6 | 2073 |
| 0.085 | 7.4 | 2067 |
| 0.055 | 4.9 | 2051 |
| 0.033 | 2.9 | 2032 |

Figure 1:
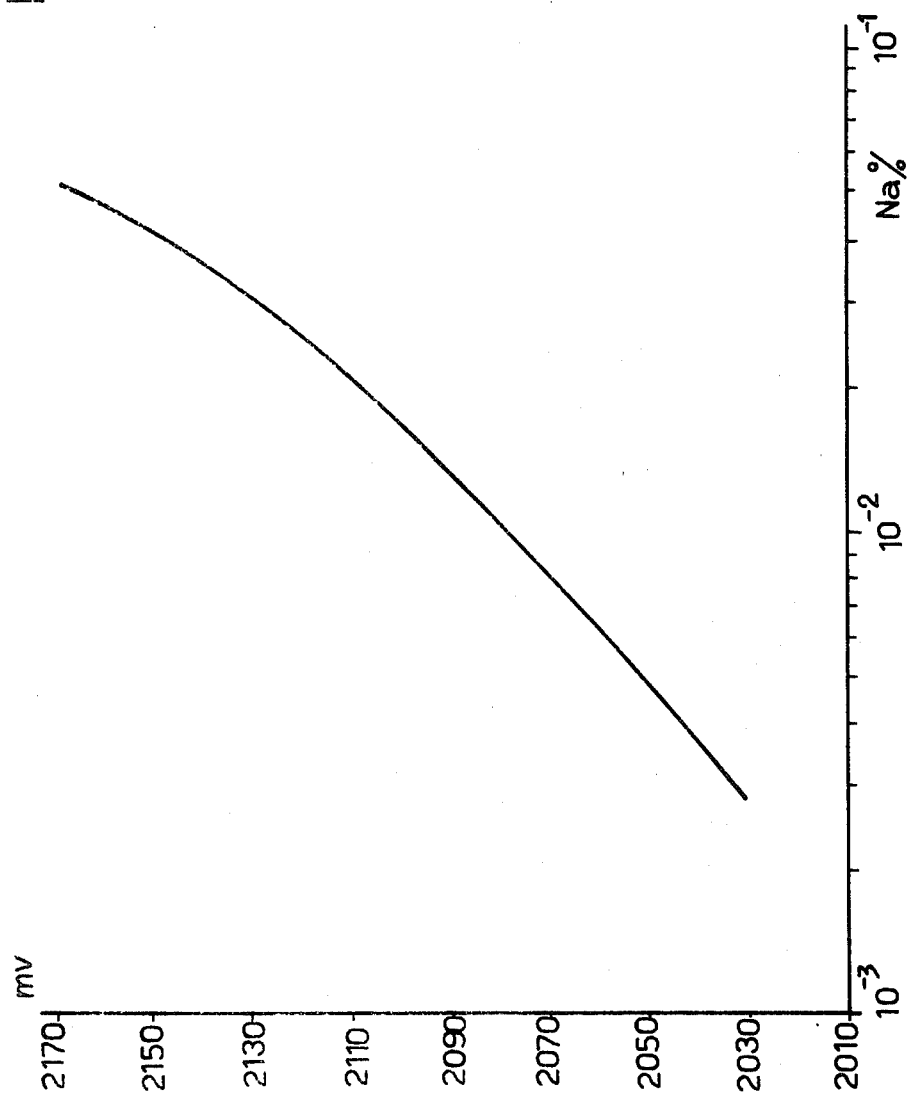
FIG. 1 is a diagram showing the e.m.f. in millivolts (plotted on a linear scale in ordinates) as a function of the molar fraction of sodium in the amalgam (plotted on a logarithmic scale) in the tests summarized in Table 4.

From the shape of the curve of FIG. 1 it is seen that it is possible to determine the concentration of sodium in the amalgam by means of measurement of the e.m.f., with great precision over the whole range of concentrations taken into consideration.

Figure 2:
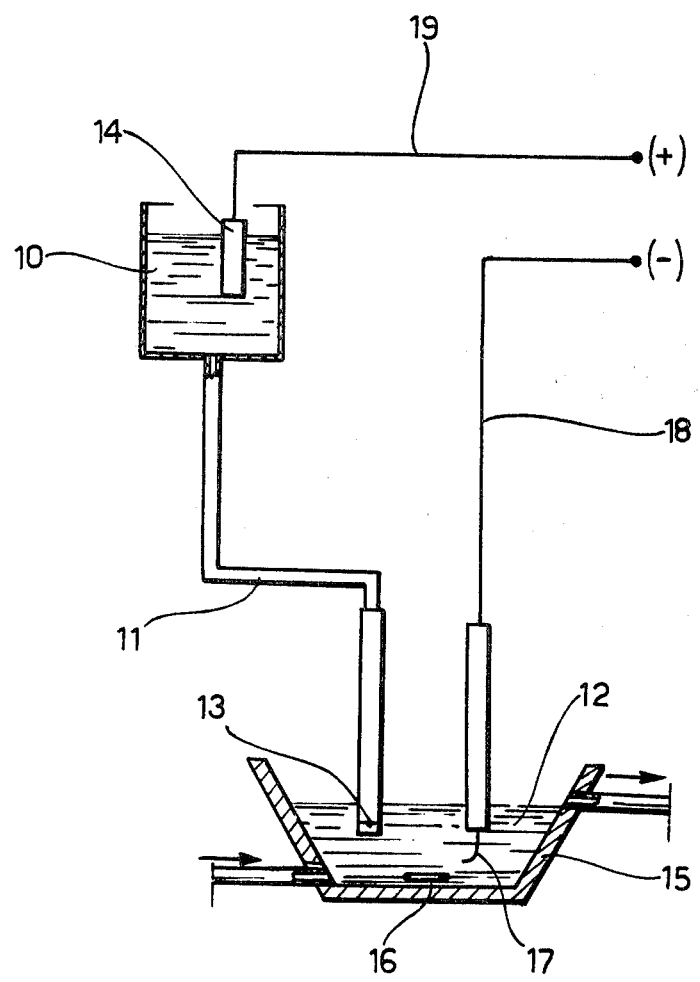
FIG. 2 shows schematically the apparatus used in the tests summarized in Tables 1–4.

The data recorded in Table 1 to 4 were obtained by using the apparatus shown schematically in FIG. 2. The electrolyte flows continuously from the container 10 through the conduit 11 and from the latter into the amalgam 12 through the porous septum 13. The reference electrode 14 is immersed in the electrolyte in the container 10. The reference electrode consists of a silver wire, surrounded by granules of silver chloride, the whole being closed in a small glass cylinder perforated to allow contact with the electrolyte.

The amalgam 12 is placed in the receptacle 15, which is provided with a jacket to bring the amalgam to the desired temperature, by means of a circulating liquid as shown. The amalgam is maintained under agitation by means of the electromagnetic agitator 16 which is suitably screened.

A platinum wire 17 is immersed in the amalgam and the terminals of the reference electrode and of the platinum wire are connected by means of wires 18 and 19 to a digital voltmeter ORION Mod.801-A, not shown in the figure.

The calomel electrode used consists of mercury and a mercury-mercurous chloride paste, with a platinum wire dipping into the mercury. The whole is enclosed in a glass phial having holes to allow contact with the electrolyte. The capillary used instead of the porous septum has been described previously.

In the tests, the feed rate of the electrolyte was equal to about 8 ml per hour for each $cm^2$ of surface area of contact.

Figure 3:
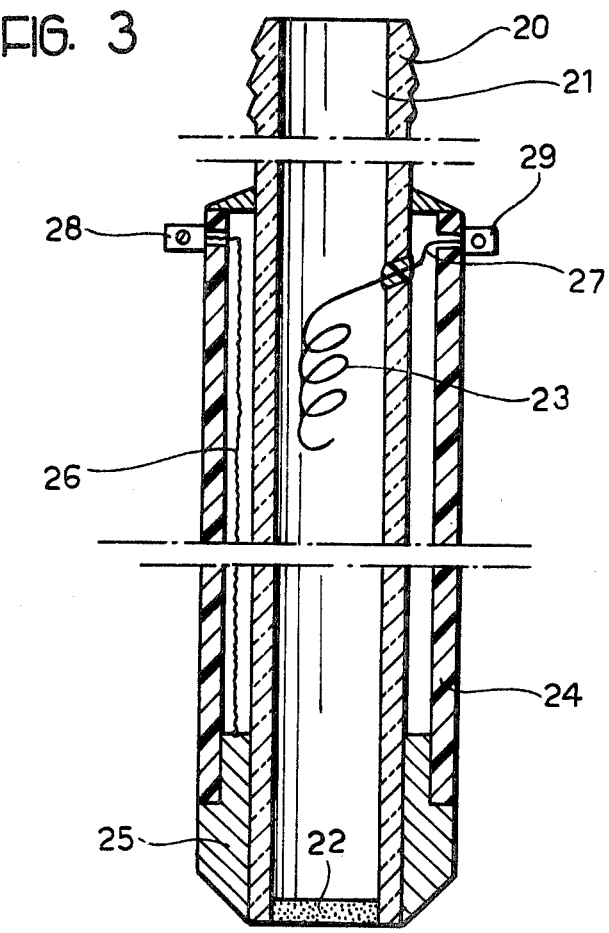
FIG. 3 shows a probe for use in the method of the invention, including the reference electrode and the conduit for the electrolyte.

The probe illustrated in FIG. 3 comprises a cylindrical body 20 of glass, or other insulating material, open at the upper end 21 and having at the lower end a porous septum 22.

Internally, in a position intermediate the two ends, is located the reference electrode 23 consisting, in the case illustrated, of a silver spiral on which silver chloride has been deposited.

The intermediate portion of the body 20 is surrounded by a sheath 24 of plastics material, for example, polypropylene.

From the lower part projects an iron ring 25 for contacting the amalgam, formed so that its upper part is sealingly inserted in the annular space between the sheath 24 and the body 20. In this annular space is housed the wire 26 which connects the ring 25 to the terminal clamp 28. A wire 27 connects the reference electrode 23 to the terminal clamp 29.

The probe conveniently has dimensions of from 2 to 3 cm in diameter and from 20 to 50 cm in length, the latter depending essentially on the apparatus with which the probe is to be used.

Figure 4:
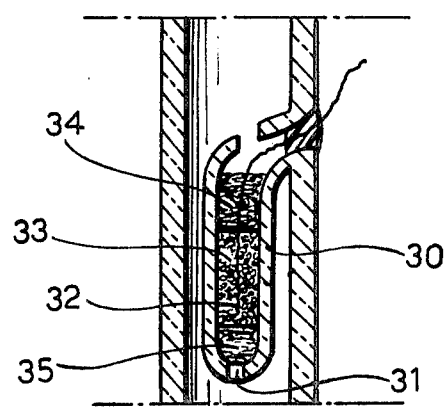
FIG. 4 shows a modification of the intermediate part of the probe of FIG. 3.

In FIG. 4 is shown a particular embodiment in which the reference electrode consists of a silver wire 32, in contact with granules of silver chloride 33. The reference electrode in housed in a container 30, generally of the same material as the body of the probe, having an aperture 31 for contact of the electrode with the electrolyte.

To avoid removal of the granules by the electrolyte, glass wool indicated 34 and 35 is conveniently inserted.

The probe is conveniently provided in its upper part with means for fixing it to the walls of the chamber in which it is to be used. In use, the probe is generally immersed in the amalgam to a depth of the order of 2–3 cm. The upper part is connected to a tube containing the electrolyte.

Figure 5:
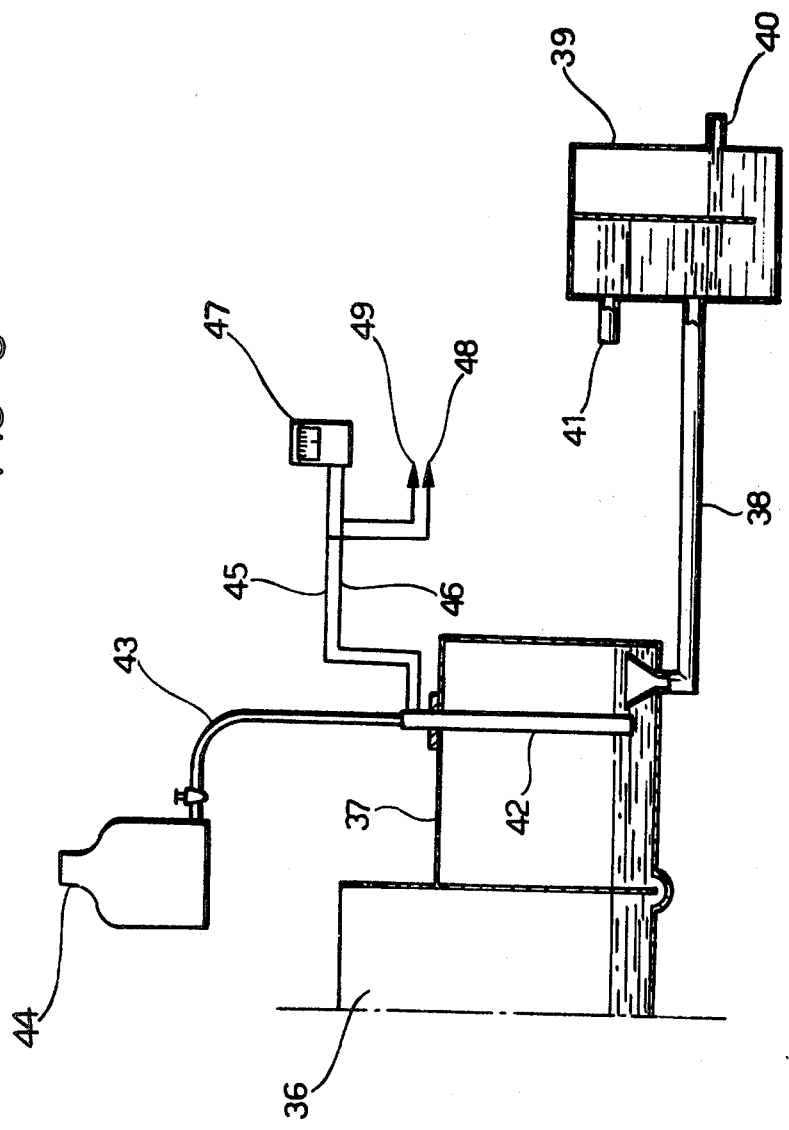
FIG. 5 shows an embodiment of an apparatus for carrying out the method of the invention, in association with a mercury-chlorine cell.

FIG. 5 shows an apparatus for carrying out the method of the invention, including the probe of FIG. 3, or of FIG. 4.

More particularly, reference 36 denotes an electrolytic cell, in which chlorine and a mercury-sodium amalgam are produced. The amalgam discharged from cell 36 flows into the chamber 37 to be washed with a small amount of water; in the figure the devices used for this washing are not shown for simplicity.

The amalgam then flows through the conduit 38 to the chamber 39, where it forms a hydraulic lock, and then to an amalgam decomposer (not shown) by means of the conduit 40, while an aqueous solution is discharged through the line 41.

The probe 42 is inserted in the chamber 37 and is immersed in the amalgam at a point close to the discharge from the said chamber. The upper end of the probe is connected by the pipe 43 to the container 44 for the electrolyte.

The wires which connect the terminals of the probe to the millivoltmeter 47 are shown as 45 and 46. The wires for connection to the process computer, designed to control the operation of the cell 36, are shown as 48 and 49.

With equipment of the type shown schematically in FIG. 5 determinations have been carried out on an industrial cell with a mercury cathode used for the production of chlorine. In particular, the probe used is of the type described in FIG. 4, having a 4P porous septum with a surface area of 1 cm². A 1 M aqueous solution of sodium chloride was made to flow through the porous septum at a rate of about 8 ml/hour. The average temperature of the amalgam was 75° C.

In table 5 are recorded the results obtained daily over the course of a month and in particular there are given the values of the e.m.f. in millivolts, the corresponding values of the sodium concentration in the amalgam determined according to the calibration curve of FIG. 2 and the same values of the concentration determined with an acidimetric method.

Table 5

| mV | % Na (weight) electrochemical measurement | % Na (weight) acidimetric measurement |
| --- | --- | --- |
| 2110 | 0.235 | 0.228 |
| 2103 | 0.204 | 0.197 |
| 2130 | 0.338 | 0.330 |
| 2124 | 0.305 | 0.300 |
| 2102 | 0.200 | 0.190 |
| 2105 | 0.213 | 0.205 |
| 2102 | 0.200 | 0.195 |
| 2103 | 0.204 | 0.200 |
| 2106.5 | 0.219 | 0.210 |
| 2080 | 0.114 | 0.106 |
| 2080 | 0.114 | 0.103 |
| 2112 | 0.245 | 0.235 |
| 2117 | 0.269 | 0.260 |
| 2114 | 0.254 | 0.247 |
| 2117 | 0.269 | 0.263 |
| 2123 | 0.300 | 0.290 |
| 2132 | 0.350 | 0.340 |
| 2147 | 0.447 | 0.435 |
| 2112 | 0.245 | 0.234 |
| 2117 | 0.269 | 0.257 |
| 2112 | 0.245 | 0.230 |
| 2090 | 0.151 | 0.148 |
| 2110.5 | 0.237 | 0.225 |
| 2119 | 0.279 | 0.270 |
| 2123 | 0.300 | 0.289 |
| 2120 | 0.284 | 0.272 |
| 2116 | 0.264 | 0.253 |
| 2123 | 0.300 | 0.287 |
| 2118.5 | 0.277 | 0.257 |
| 2138 | 0.386 | 0.366 |
| 2140 | 0.398 | 0.372 |

What we claim is:

1. A method for continuously measuring the sodium metal concentration in a flow of mercury-sodium amalgam, which comprises continuously flowing an aqueous solution of sodium chloride through a conduit of electrically insulating material terminating with a porous member immersed in the flow of the mercury-sodium amalgam, said solution being passed through said conduit at a rate such as to ensure continuous renewal of the interface between the solution and the amalgam and of at least 4 mil per hour and per cm² of surface area of contact between the surface of the porous member and the amalgam, and monitoring the electromotive force generated between said amalgam and a calomel or silver-silver chloride reference electrode located within said conduit and in contact with said solution, said sodium metal concentration being a univocal function of said electromotive force.

2. The method of claim 1, wherein the concentration of sodium chloride in said solution is from 0.01 M to the saturation value of the operating temperature.

3. The method of claim 1, wherein said mercury-sodium amalgam is the process amalgam from a mercury-chlorine cell.

4. The method of claim 1, wherein said amalgam has a nominal concentration of sodium of from 0.15 to 0.50% by weight.

5. The method of claim 1, wherein said amalgam has a nominal concentration of sodium of from 0.2 to 0.3% by weight.

6. The method of claim 1, wherein the concentration of sodium chloride in said solution is substantially 1 M.

7. The method of claim 1, wherein said solution flows at a rate of the order of 8 ml per hour and per cm³ of the said surface of contact.

8. The method of claim 1, wherein said reference electrode is a calomel reference electrode.

9. The method of claim 1, wherein said reference electrode is silver-silver chloride.

10. The method of claim 1, wherein said porous member is a porous septum.

11. The method of claim 8, wherein said porous septum has a surface area of about 1 cm².

12. The method of claim 10, wherein said porous septum has pores of from 3 to 150 microns.

13. The method of claim 1, wherein said porous member is a porous capillary.

14. The method of claim 13, wherein said capillary opening has a diameter of from 0.3 to 1 mm.

* * * * *